US009759669B2

(12) United States Patent
Jingu (10) Patent No.: US 9,759,669 B2
(45) Date of Patent: Sep. 12, 2017

(54) INSPECTION DEVICE (71) Applicant: Hitachi High-Technologies Corporation, Minato-ku, Tokyo (JP)

(72) Inventor: Takahiro Jingu, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 71 days.

(21) Appl. No.: 14/416,752

(22) PCT Filed: Jul. 3, 2013

(86) PCT No.: PCT/JP2013/068200
§ 371 (c)(1),
(2) Date: Jan. 23, 2015

(87) PCT Pub. No.: WO2014/017264
PCT Pub. Date: Jan. 30, 2014

(65) Prior Publication Data
US 2015/0177161 A1 Jun. 25, 2015

(30) Foreign Application Priority Data

Jul. 24, 2012 (JP) ................................ 2012-163222

(51) Int. Cl.
*G01N 21/01* (2006.01)
*G01N 21/88* (2006.01)
(Continued)

(52) U.S. Cl.
CPC ......... *G01N 21/9501* (2013.01); *G01N 21/01* (2013.01); *G01N 21/88* (2013.01);
(Continued)

(58) Field of Classification Search
USPC .... 356/237.1–237.6, 242.1–243.8, 426–431, 356/600–640
See application file for complete search history.

(56) References Cited

U.S. PATENT DOCUMENTS 5,352,636 A * 10/1994 Beinglass ........... C23C 16/0218
148/DIG. 17
5,611,886 A * 3/1997 Bachman ................ B05C 11/08
118/52
(Continued)

FOREIGN PATENT DOCUMENTS

JP      9-213637 A    8/1997
JP   2000-131028 A    5/2000
(Continued)

OTHER PUBLICATIONS

English translation of First Office Action issued in counterpart Japanese Application No. 2012-163222 dated Feb. 19, 2016 (3 pages).
(Continued)

*Primary Examiner* — Tri Ton
*Assistant Examiner* — Jarreas C Underwood
(74) *Attorney, Agent, or Firm* — Crowell & Moring LLP (57) ABSTRACT

In an inspection apparatus, inspection is carried out by linearly moving a wafer while rotating the wafer with respect to light. In a case where the wafer is rotated, the velocity of flow of air in outer regions of the wafer is increased, and there is a possibility that the flow of the air in the outer regions cause particles contained in an atmosphere in the vicinity of the wafer to be adhered to the wafer. In a case where such particles are adhered to the wafer, the particles are also detected as a defect, and therefore yields and cleanliness in a semiconductor production process cannot be correctly evaluated. Therefore, it is desirable that adhesion of the particles contained in the atmosphere in the vicinity of the wafer to the wafer be reduced as much as possible. Further, it is expected that, when, for example, rotation speed of the wafer is increased or a diameter of the wafer is increased, such particles are adhered further remarkably. This point has not been satisfactorily considered (Continued)

in the conventional arts. The invention has a feature that a conductor such as a draft to outer regions is supplied from above a substrate while the substrate is being rotated and the supplied conductor is exhausted on outside of the substrate.

18 Claims, 11 Drawing Sheets (51) Int. Cl.
*H01L 21/67* (2006.01)
*G01N 21/95* (2006.01)
*G01N 21/94* (2006.01)

(52) U.S. Cl.
CPC ....... *G01N 21/94* (2013.01); *H01L 21/67288* (2013.01); *G01N 2201/063* (2013.01)

(56) References Cited

U.S. PATENT DOCUMENTS

| | | | | |
|---|---|---|---|---|
| 5,931,721 | A * | 8/1999 | Rose | B08B 7/0092 451/39 |
| 6,135,862 | A * | 10/2000 | Ukai | B23Q 11/0042 409/136 |
| 6,274,878 | B1 * | 8/2001 | Li | H01L 21/67259 250/222.1 |
| 6,415,804 | B1 | 7/2002 | Pascal et al. | |
| 6,541,376 | B2 * | 4/2003 | Inada | G03F 7/162 438/618 |
| 6,566,169 | B1 * | 5/2003 | Uziel | B08B 7/0042 216/65 |
| 6,630,995 | B1 | 10/2003 | Hunter | |
| 6,795,164 | B2 * | 9/2004 | Hoogenraad | G03F 9/7011 355/53 |
| 8,125,654 | B2 * | 2/2012 | Benvegnu | B24B 37/013 356/630 |
| 8,216,382 | B2 * | 7/2012 | Shindo | B08B 7/0042 134/1 |
| 8,334,222 | B2 * | 12/2012 | Gotou | H01L 21/02049 257/E21.001 |
| 8,409,354 | B2 * | 4/2013 | Chiang | C23C 16/45544 118/715 |
| 8,718,810 | B2 * | 5/2014 | Benvegnu | B24B 37/013 700/121 |
| 2002/0098283 | A1 * | 7/2002 | Gurer | B05C 5/0208 427/240 |
| 2002/0127334 | A1 | 9/2002 | Gurer et al. | |
| 2004/0112018 | A1 | 6/2004 | Vuijk | |
| 2006/0062897 | A1 * | 3/2006 | Gu | C23C 18/1632 427/8 |
| 2007/0294066 | A1 | 12/2007 | Nakayama et al. | |
| 2009/0084409 | A1 * | 4/2009 | Okura | B08B 3/02 134/21 |
| 2009/0122293 | A1 * | 5/2009 | Shibazaki | G03F 7/70716 355/73 |
| 2009/0152381 | A1 | 6/2009 | Kikuchi | |
| 2010/0124610 | A1 * | 5/2010 | Aikawa | C23C 16/4584 427/255.28 |

FOREIGN PATENT DOCUMENTS

| | | |
|---|---|---|
| JP | 2003-518735 A | 6/2003 |
| JP | 2004-527112 A | 9/2004 |
| JP | 2004-528087 A | 9/2004 |
| JP | 2004-531879 A | 10/2004 |
| JP | 2005-136249 A | 5/2005 |
| JP | 2005-309999 A | 11/2005 |
| JP | 2005-327906 A | 11/2005 |
| JP | 2006-352099 A | 12/2006 |
| JP | 2008-263048 A | 10/2008 |
| JP | 2008-296069 A | 12/2008 |
| JP | 2009-16595 A | 1/2009 |
| JP | 2009-142750 A | 7/2009 |
| JP | 2009-246163 A | 10/2009 |
| JP | 2010-236948 A | 10/2010 |

OTHER PUBLICATIONS

International Search Report (PCT/ISA/210) dated Aug. 20, 2013 with English translation (five pages), PCT/JP2013/068200.
Korean-language Office Action issued in counterpart Korean Application No. 10-2015-7001476 dated Mar. 28, 2016 with English translation (Fifteen (15) pages).
Japanese-language Office Action issued in counterpart Japanese Application No. 2012-163222 dated Sep. 13, 2016 with English translation (Six (6) pages).
Korean Office Action issued in counterpart Korean Application No. 10-2015-7001476 dated Oct. 28, 2016 with English-language translation (eight (8) pages).
Korean-language Office Action issued in counterpart Korean Application No. 10-2015-7001476 dated Jan. 12, 2017 with English translation (11 pages).

* cited by examiner

INSPECTION DEVICE

TECHNICAL FIELD

The present invention relates to an inspection apparatus, a cleaning technique of a substrate, and a draft control technique. In particular, the invention relates to an inspection apparatus for inspecting a defect on a substrate such as a semiconductor wafer, a cleaning technique, and a draft control technique.

BACKGROUND ART

In a semiconductor production process, particles and defects such as scratches on a surface of a semiconductor substrate (wafer) cause failure such as insufficient insulation, short, and the like of wiring formed on the wafer and also cause insufficient insulation of a capacitor and breakage of a gate oxide film and the like. Therefore, in the semiconductor production process, it is important to detect a defect on a surface of a wafer and feedback the defect to the semiconductor production process.

A so-called inspection apparatus detects such a defect. As an example of the inspection apparatus, there is an optical inspection apparatus that detects a defect on a substrate by irradiating a substrate with light and detecting scattered light thereof. The optical inspection apparatus is broadly classified into two types, i.e., a surface inspection apparatus for inspecting a mirror wafer and a patterned wafer inspection apparatus for inspecting a wafer on which a circuit pattern is formed.

In particular, in a case of the mirror wafer inspection apparatus, it is known that inspection is carried out by linearly moving a wafer while rotating the wafer with respect to light. The following PTLs 1-8 are cited as conventional arts regarding an inspection apparatus and draft control.

CITATION LIST

Patent Literatures

PTL 1: JP-A-2005-327906
PTL 2: JP-T-2004-531879
PTL 3: JP-T-2004-527112
PTL 4: JP-T-2003-518735
PTL 5: JP-A-2009-142750
PTL 6: JP-A-2005-309999
PTL 7: JP-T-2004-528087
PTL 8: JP-A-2010-236948

SUMMARY OF INVENTION

Technical Problem

As described above, in a mirror wafer inspection apparatus, inspection is carried out by linearly moving a wafer while rotating the wafer with respect to light. In a case where the wafer is rotated, the velocity of flow of air in outer regions of the wafer is increased, and there is a possibility that the flow of the air in the outer regions cause particles contained in an atmosphere in the vicinity of the wafer to be adhered to the wafer. In a case where such particles are adhered to the wafer, the particles are also detected as a defect, and therefore yields and cleanliness in a semiconductor production process cannot be correctly evaluated. Therefore, it is desirable that adhesion of the particles contained in the atmosphere in the vicinity of the wafer to the wafer be reduced as much as possible. Further, it is expected that, when, for example, rotation speed of the wafer is increased or a diameter of the wafer is increased, such particles are adhered further remarkably. This point has not been satisfactorily considered in the conventional arts.

Solution to Problem

The invention has a feature that a conductor such as a draft to outer regions is supplied from above a substrate while the substrate is being rotated and the supplied conductor is exhausted on outside of the substrate.

Advantageous Effects of Invention

According to the invention, it is possible to reduce the number of particles adhered to a substrate in comparison with conventional arts.

DESCRIPTION OF EMBODIMENTS

Hereinafter, examples of the invention will be described with reference to drawings.

Example 1

Figure 1:
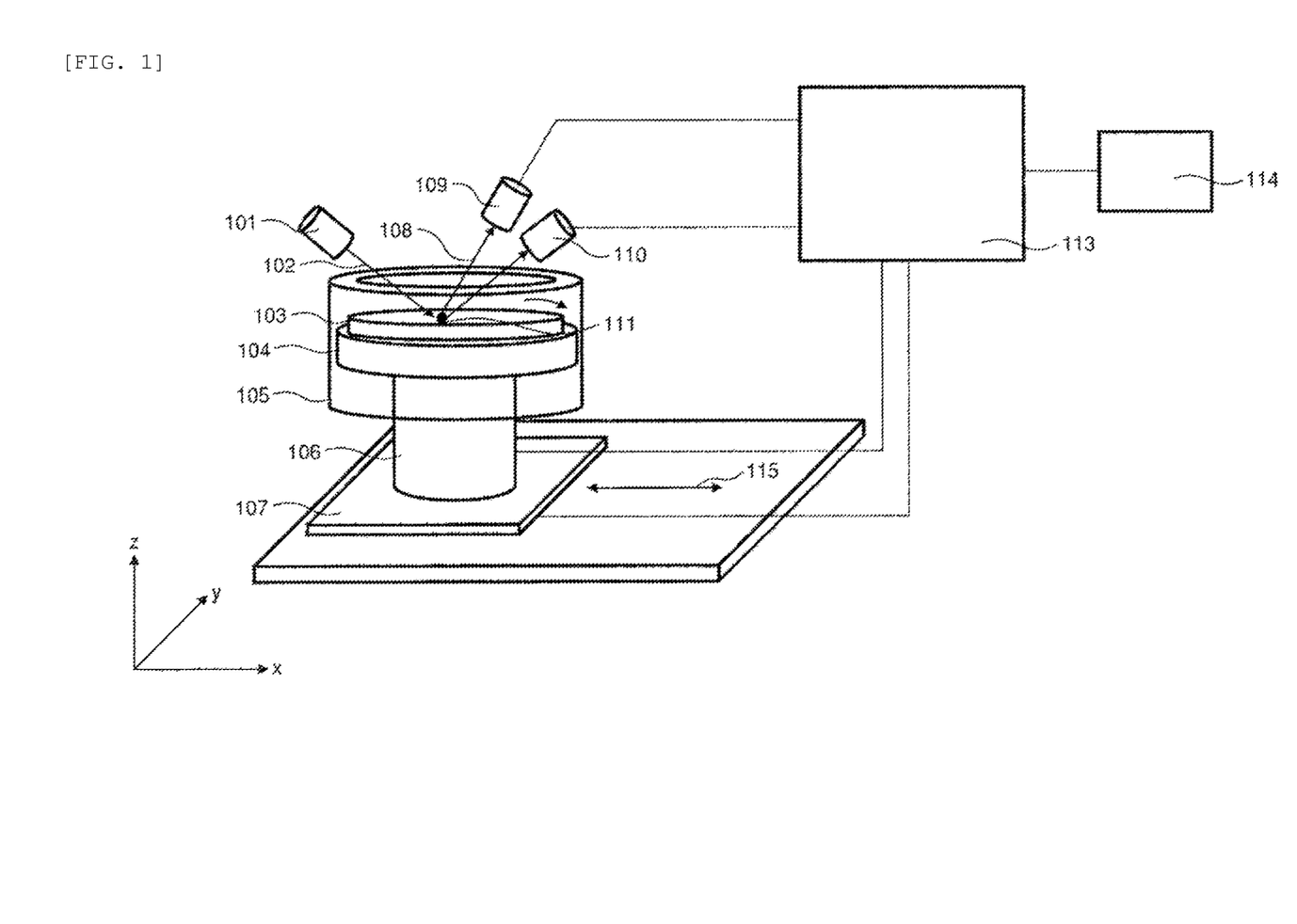
FIG. 1 illustrates an inspection apparatus of Example 1.

FIG. 1 illustrates an inspection apparatus of this example. An illumination optical system 101 irradiates a substrate 103 with illumination light such as a laser beam to form an illuminated region 111 on the substrate 103. Scattered light 108 generated from the illuminated region 111 is detected by detection optical systems 109 and 110. Each of the detection optical systems 110 and 109 includes an objective lens, an imaging lens, an optoelectronic device (photomultiplier, one-dimensional CCD, two-dimensional CCD (including TDI), avalanche photodiode, and the like) (the detection optical system 110 similarly includes them). Electrical signals from the detection optical systems 109 and 110 are transmitted to an processing unit 113 via an A/D converter and the like. In the processing unit 113, the electrical signals from the detection optical systems 109 and 110 are subjected to threshold processing with the use of a threshold. In a case where the electrical signals are equal to or less than the threshold, it is determined that the electrical signals indicate false. In a case where the electrical signals are larger than the threshold, it is determined that the electrical signals indicate defect. Note that, regarding the threshold processing, the electrical signals from the detection optical systems 109 and 110 are added and the added signals are subjected to the threshold processing in some cases or each of the electrical signals is subjected to the threshold processing in some cases.

The substrate 103 is mounted on a substrate mounting unit 104. The substrate 103 is attached to the substrate mounting unit 104 with a back surface attachment method in which a whole back surface of the substrate 103 is attached to the substrate mounting unit 104 in some cases or with a so-called edge grip method in which only an end portion of the substrate 103 is held by the substrate mounting unit 104 instead of attaching the back surface thereof in some cases. The substrate mounting unit 104 is mounted on a spindle 106 for rotating the substrate mounting unit 104. In a case where the spindle 106 is rotated, the substrate 103 is also rotated. The spindle 106 is mounted on a stage 107 capable of moving in X and Y directions or in an X direction and capable of moving upward and downward in a Z direction. That is, the substrate 103 is rotated by the spindle 106 and is moved by the stage 107 in a direction indicated by an arrow 115. By this operation, the illuminated region 111 spirally scans relatively on the substrate 103. By this scanning, a whole surface of the substrate 103 is inspected. Note that a moving distance of the stage and a rotation angle of the spindle are transmitted to the processing unit 113. Therefore, the processing unit 113 can associate a result of the inspection with coordinates (polar coordinates) on the substrate, the coordinates being obtained on the basis of the moving distance and the rotation angle. The result of the inspection associated with the coordinates on the substrate is displayed on a monitor unit 114 as a map.

Figure 2:
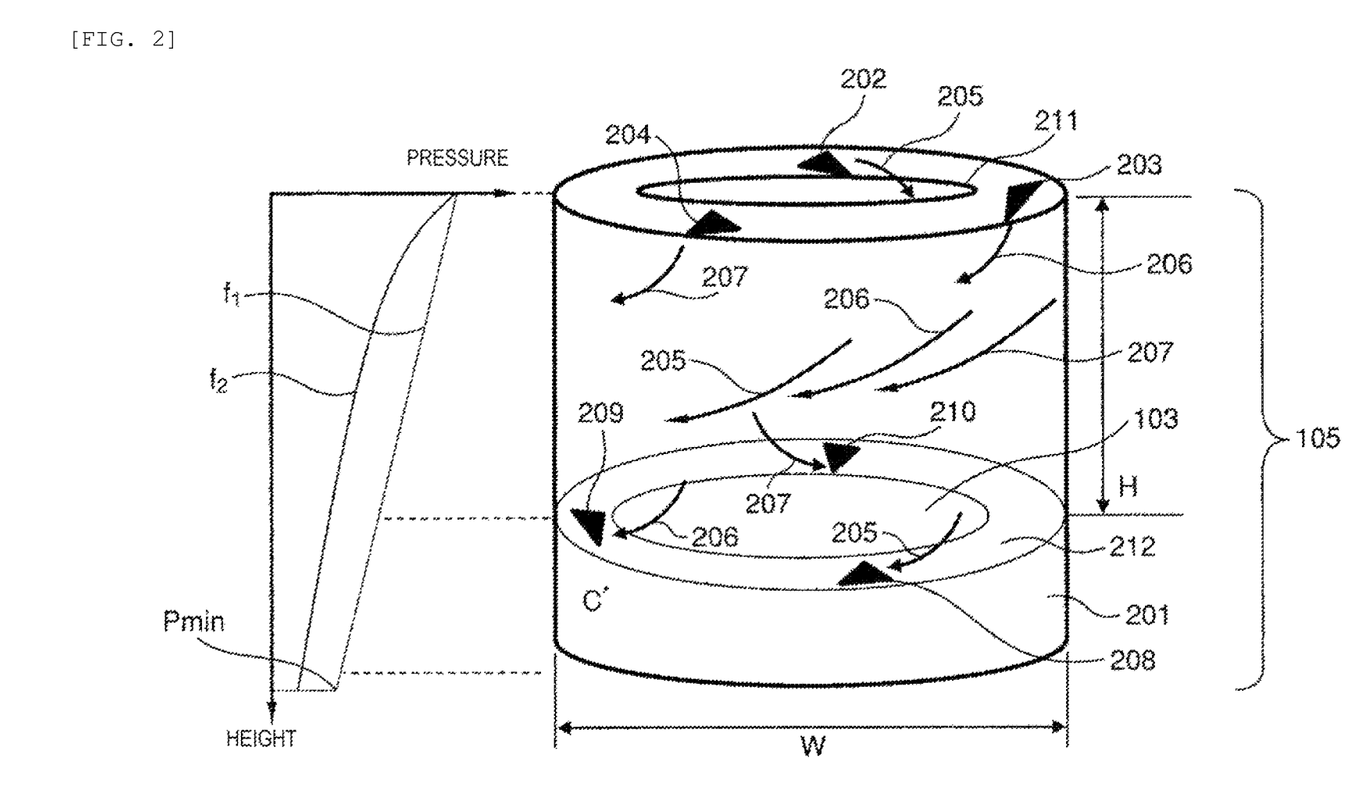
FIG. 2 illustrates details of a chamber system 105.

In this example, the inspection apparatus includes a chamber system 105 covering at least the substrate 103. Details of the chamber system 105 will be described with reference to FIG. 2. FIG. 2 illustrates the details of the chamber system 105. The chamber system 105 includes a chamber part for covering at least the substrate 105, a supply system for supplying a conductor such as gas, and an exhaust system for exhausting the supplied conductor.

In FIG. 2, the chamber part is indicated as a chamber 201. The chamber 201 covers at least the substrate 103 and has a substantially circular cylinder shape. An aperture 211 is provided in an upper portion of the chamber 201. Illumination light 102 from the illumination optical system 101 is supplied to the substrate 103 through the aperture 211, and the scattered light 108 is detected by the detection optical systems 109 and 110 also through the aperture 211. Note that, instead of the aperture 211, an upper surface of the chamber 201 may be made from an optically transparent material.

Figure 3:
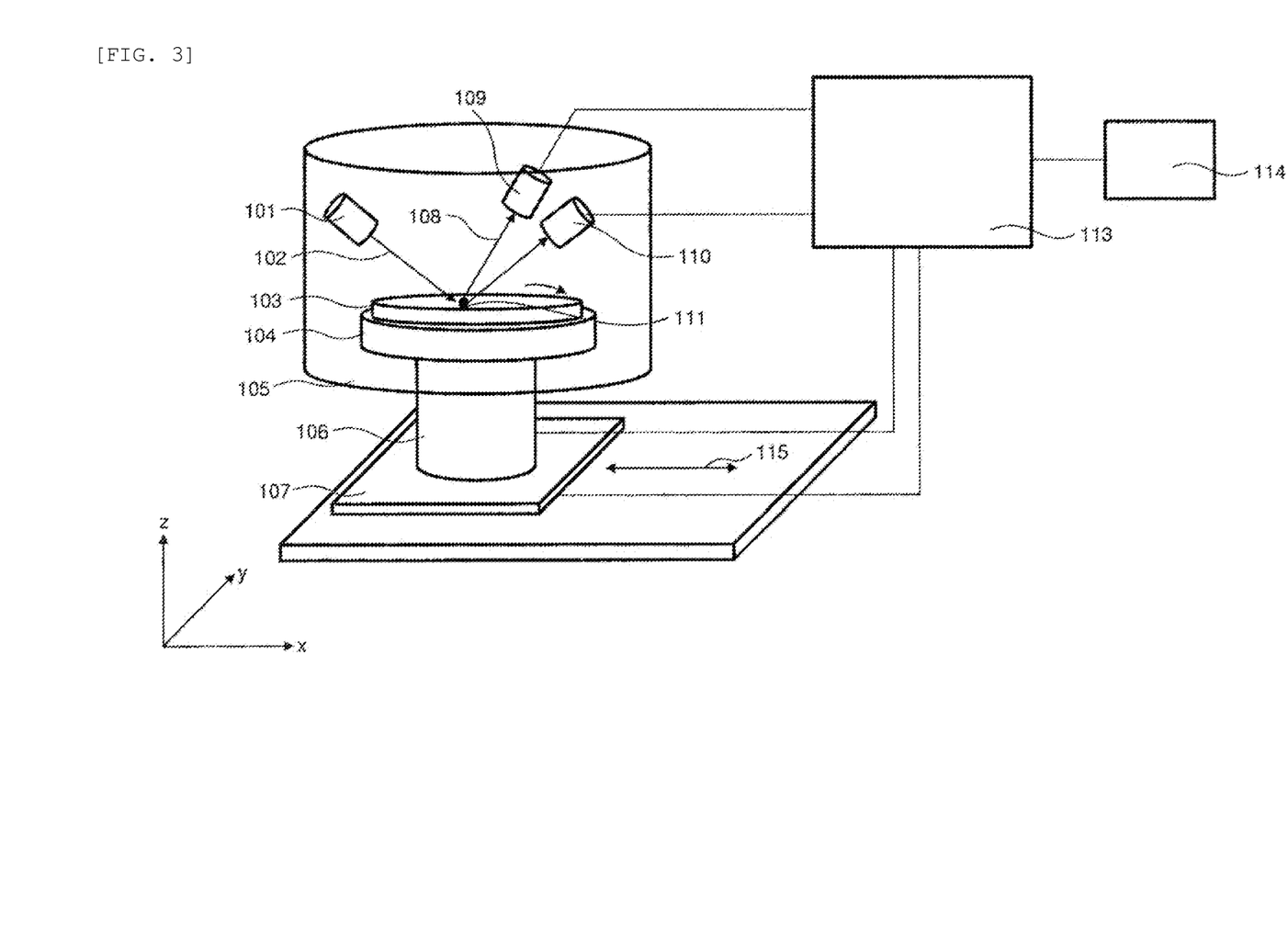
FIG. 3 illustrates a modification example of a chamber system.

Note that a size of the chamber system 105 is determined on the basis of required cleanliness and a size of the substrate 103 in some cases. Therefore, in a case where a required size of the chamber system 105 is large, as illustrated in FIG. 3, the chamber system 105 accommodates the illumination optical system 101 and the detection optical systems 109 and 110 in some cases. Further, the chamber system 105 does not have the aperture 211 in some cases.

Note that there is a case where guides are provided in an inner surface of the chamber 201 in order to reduce friction of drafts 205, 206, and 207 (described below). There is also a case where protrusions or the like are provided, i.e., projections and pits are substantially provided in the inner surface of the chamber 201 in order to reduce the friction of the drafts 205, 206, and 207 (described below). As a matter of course, the inner surface of the chamber 201 is substantially flat in some cases.

Figure 4:
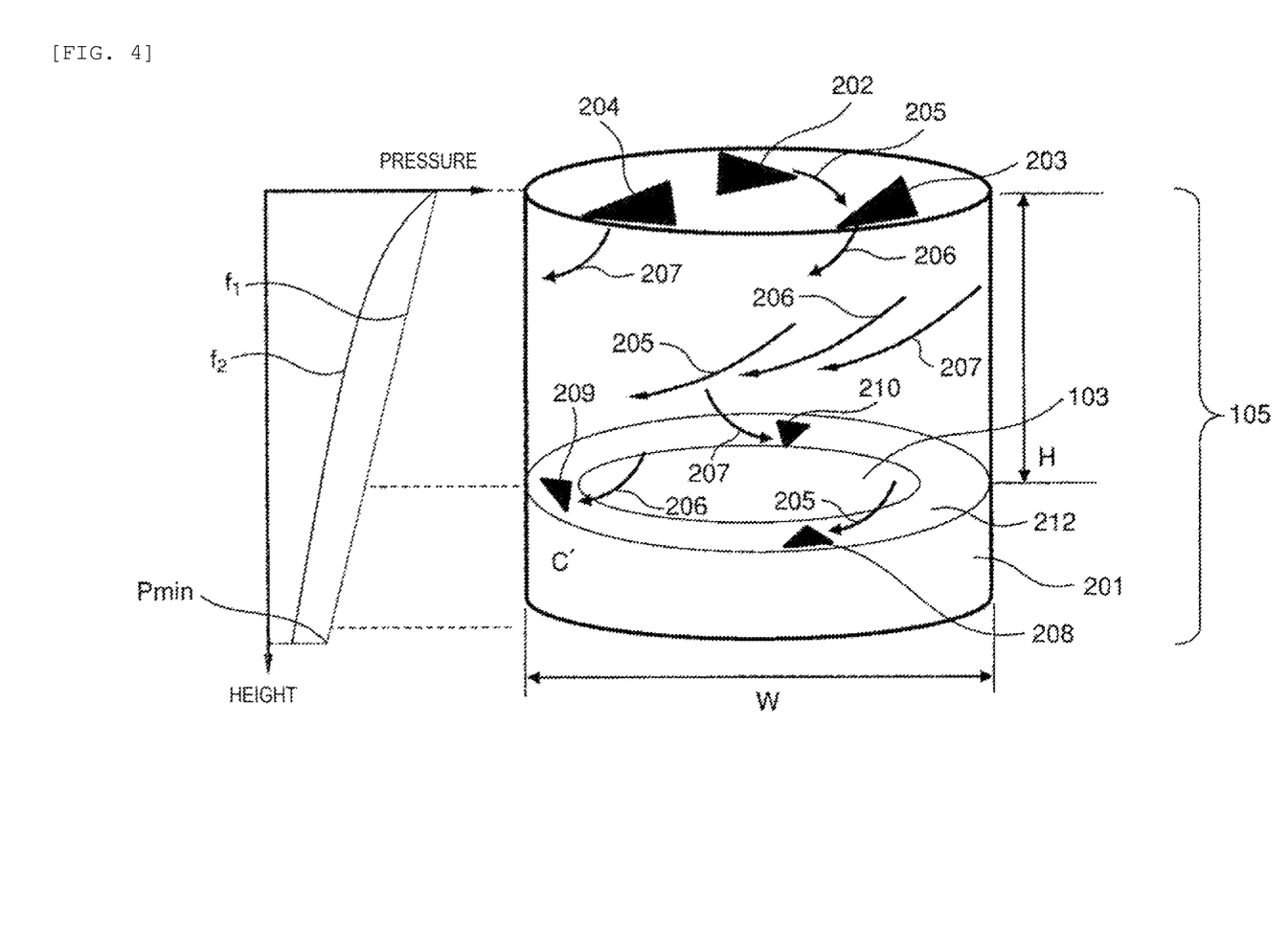
FIG. 4 illustrates details of a chamber system 105 that does not have an aperture 211.

Supply systems will be described below. The supply systems are indicated as, for example, draft supply units 202, 203, and 204 in FIGS. 2 and 4. In FIG. 2, the draft supply units 202, 203, and 204 are located outside the aperture 211 on the upper surface of the chamber 201. In FIG. 4, because there is no aperture portion on the upper surface, the draft supply units 202, 203, and 204 are located at more preferable positions to perform draft control in comparison with a case of FIG. 2.

The draft supply units 202, 203, and 204 supply a conductor such as gas into the chamber 201. As the gas to be supplied, air may be employed, or inert gas such as nitrogen and argon may be employed. The gas supplied from the draft supply units 202, 203, and 204 is indicated as the drafts 205, 206, and 207 in FIGS. 2 and 4.

Figure 5:
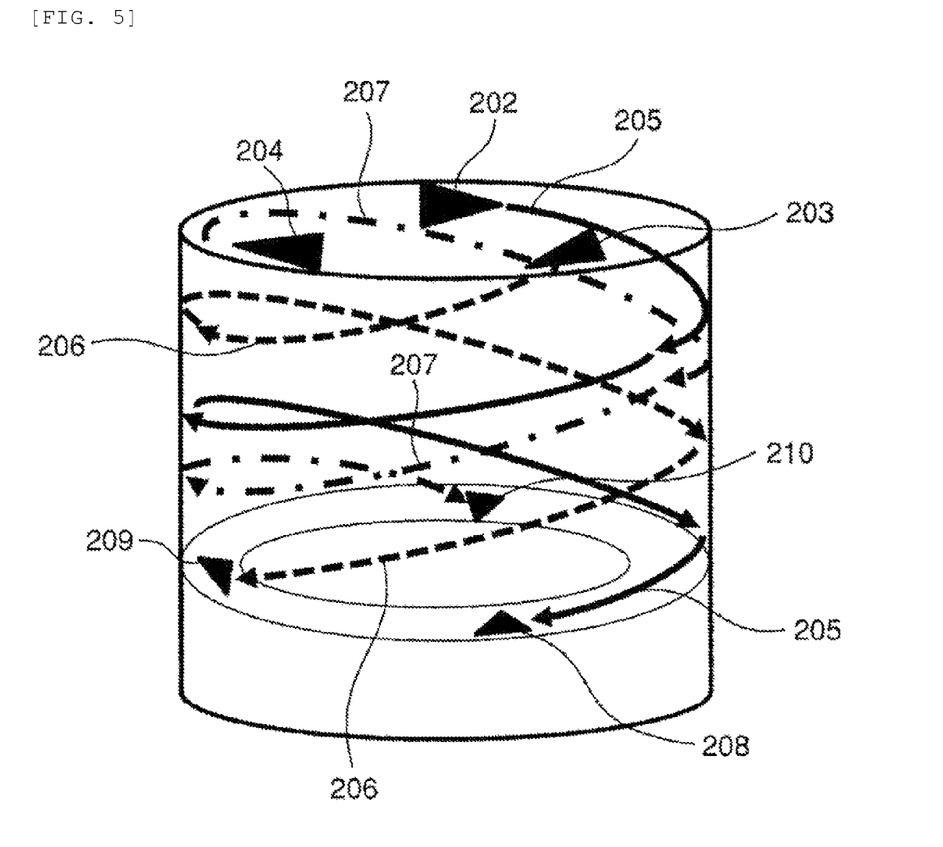
FIG. 5 illustrates a flow of a draft.

More specifically, as illustrated in FIG. 5, the drafts 205, 206, and 207 are spirally fallen while forming independent and different laminar flows in an internal space along a side surface of the chamber 201 and are supplied to the outer regions from above the substrate 103. The outer regions can be expressed in various ways, and, for example, can be expressed as positions closer to the end portion of the substrate 103 than to a center of the substrate 103. Note that, in this case, paths of the respective drafts 205, 206, and 207 are not overlapped with one another. That is, the drafts do not generate turbulence and are supplied to the substrate 103 while forming different laminar flows. Directions of the drafts 205, 206, and 207 (more specifically, directions of loci at the time of projecting the drafts 205, 206, and 207 onto the substrate 103) are the same as a direction in which the substrate 103 is rotated. The drafts 205, 206, and 207 supplied to the outer regions of the substrate 103 are exhausted by draft exhaust units 208, 209, and 210, respectively, to outside of the chamber 201.

Exhaust systems will be described below. The exhaust systems are indicated as, for example, the draft exhaust units 208, 209, and 210 in FIGS. 2 and 4. The draft exhaust units 208, 209, and 210 are located at different positions on a shield plate 212 provided between the substrate 103 and the substrate mounting unit 104. The drafts 205, 206, and 207 supplied to the outer regions of the substrate 103 are exhausted by the draft exhaust units 208, 209, and 210, respectively, to the outside of the chamber 201.

Note that there is a case where protrusions or the like are provided, i.e., projections and pits are substantially provided in a surface of the shield plate 212 in order to reduce the friction of the drafts 205, 206, and 207 to be exhausted. As a matter of course, the surface of the shield plate 212 is substantially flat in some cases.

Pressure distribution in the chamber 201 will be described below. A relationship between a height direction of the substrate 103 and a pressure in the chamber 201 is indicated as a linear function $f_1$ in FIGS. 2 and 4. That is, by supplying the drafts 205, 206, and 207, the distribution is such that the pressure in the chamber 201 becomes higher in an upward direction of the chamber 201 and becomes lower in a lower portion of the chamber 201. Note that, in this case, a minimum value Pmin of the pressure is controlled to be higher than that on the outside of the chamber 201. By setting the minimum value as described above, it is possible to prevent air from flowing from the outside. The pressure distribution may be a function $f_2$ whose degree is higher than the linear function, instead of the linear function $f_1$.

Figure 6:
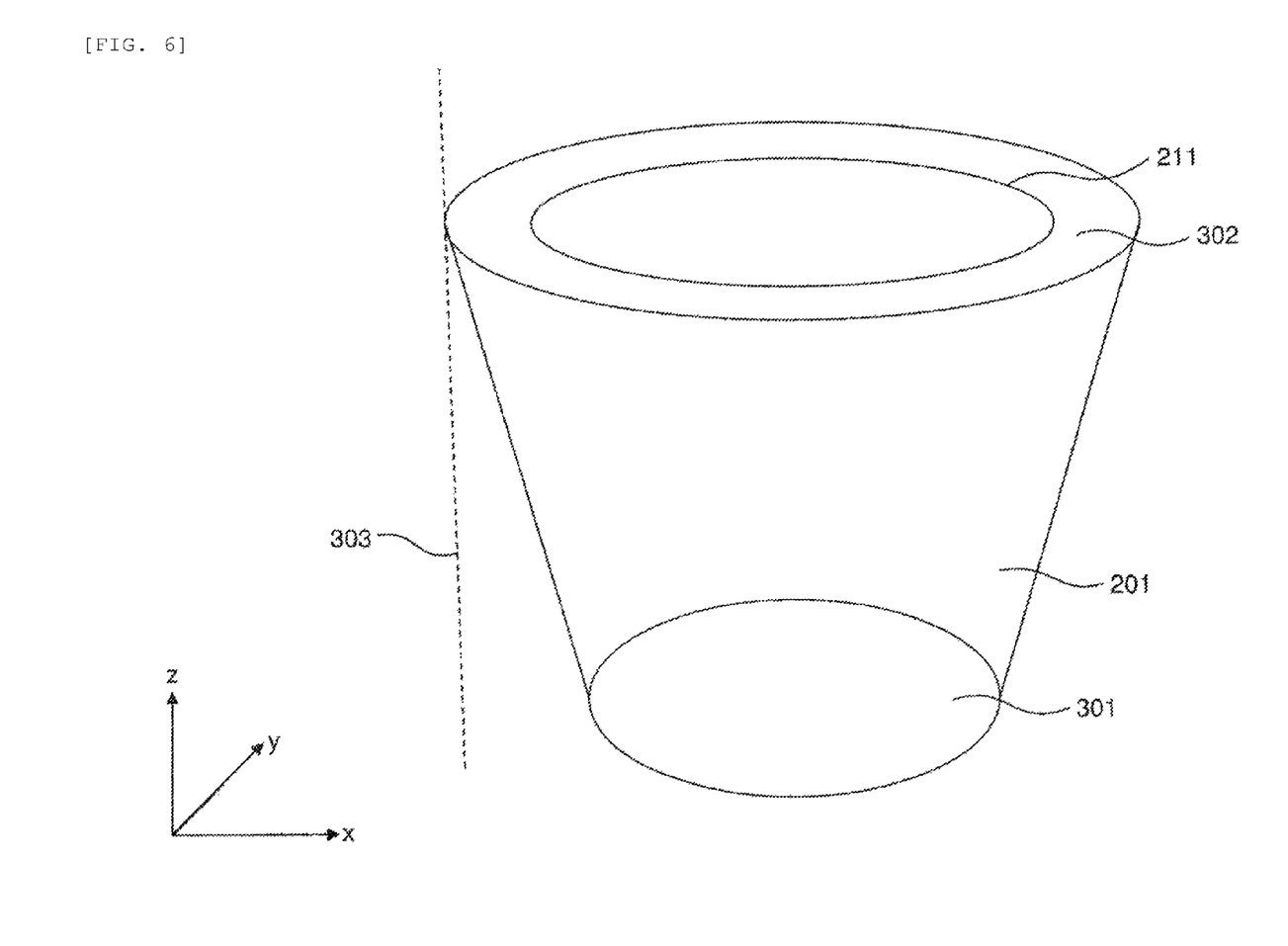
FIG. 6 illustrates a cone-shaped chamber 201.

Note that the chamber 201 may have other shapes. As illustrated in FIG. 6, an area of a lower surface 301 of the chamber 201 does not need to be the same as an area of the upper surface 302. That is, the chamber 201 may have a substantially cone shape. In a case where the chamber 201 has the substantially cone shape, the side surface of the chamber is inclined with respect to a normal line 303 of the substrate 103. In a case where the chamber 201 has the substantially cone shape, it is possible to improve the velocity of flows of the drafts 205, 206, and 207 in a case where the drafts 205, 206, and 207 are supplied to the outer regions of the substrate 103. Note that the chamber 201 in FIG. 6 also does not have the aperture 211 in some cases.

A relationship between the illumination light 102 and a height H (as another expression, a length between the substrate 103 and the upper portion of the chamber 201) of the chamber 201 will be described below. As illustrated in FIG. 1, the illumination light 102 is obliquely incident on the substrate 103 at a certain incident angle. At this time, it is desirable in some cases that the incident angle be substantially a Brewster's angle. Therefore, it is desirable in some cases that the chamber 201 have the height H at which the substrate 103 can be illuminated with the illumination light 102 at the Brewster's angle. Further, the Brewster's angle is a function of a reflective index on an incident side and a reflective index on a transmission side. In this example, as described above, as the gas to be supplied, not only air but also inert gas such as nitrogen and argon may be used. The substrate 103 to be inspected is in some cases a so-called mirror wafer or a substrate in which a certain film is formed on the mirror wafer. This means that at least one of the reflective index on the incident side and the reflective index on the transmission side is changed in a process of inspection, i.e., the Brewster's angle is changed. In view of this, this example may be structured to change the height H of the chamber 201 in accordance with a change of the Brewster's angle with the use of change means (e.g., combination of a rail and a block) for changing a relative distance between the substrate 103 and the chamber 201. Further, at least one of a flow rate and the velocity of flow of gas to be supplied may be changed in accordance with a change of the height of the chamber 201.

Figure 7:
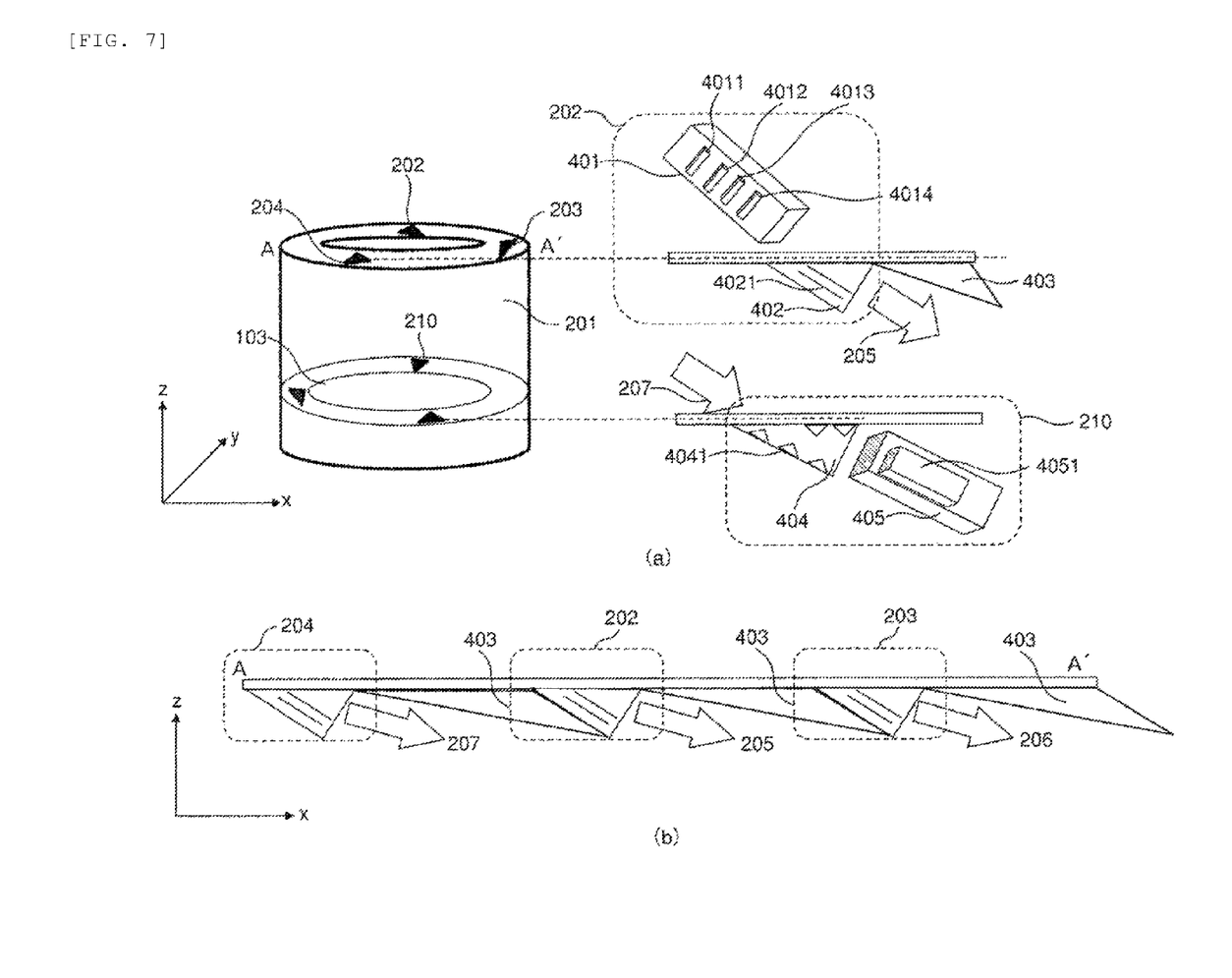
FIGS. 7A and 7B illustrate details of a draft supply unit 202 and a draft exhaust unit 210.

Details of the draft supply unit 202 and the draft exhaust unit 210 will be described below with reference to FIG. 7. FIG. 7 (a) illustrates details of the draft supply unit 202 and the draft exhaust unit 210, and FIG. 7(b) illustrates the draft supply unit 202 and the draft exhaust unit 210 from an A-A' cross-section of the chamber 201. When observed from above the substrate 103, the draft supply units 202, 203, and 204 are located to surround the substrate 103. The same applies to the draft exhaust unit 210. Outlet ports of the draft supply units 202, 203, and 204 are directed in a circumference direction of the substrate. The same applies to an exhaust port of the draft exhaust unit 210.

The draft supply unit 202 will be described in more detail. The draft supply unit 202 includes a gas supply unit 401 and a duct 402 that is a supply port. The gas supply portion 401 includes a gas source 4011 for supplying air, nitrogen, argon, or the like, a control portion 4012 for controlling at least one of a flow rate and the velocity of flow of gas, a dehumidification portion 4013 for controlling a dew point of the gas, and a filtering portion 4014 for removing particles from the gas. The gas controlled in terms of at least one of the flow rate and the velocity of the flow, humidity, and cleanliness is supplied, as the draft 205, to the inner surface of the chamber 201 at a predetermined angle from the gas supply unit 401 through the duct 402. Note that the duct 402 is inclined with respect to the upper surface of the chamber 201 so as to efficiently supply the gas to the chamber 201, and a guide 4021 for rectifying the gas is provided in the duct 402.

Note that protrusions 403 or the like or projections and pits are substantially provided in order to reduce the friction of the draft 205 in an inner surface and a side surface of the upper surface of the chamber 201.

Details of the draft exhaust unit 210 will be described below. The draft exhaust unit 210 includes a duct 404 that is an exhaust port and an exhaust source 405 such as a pump. The duct 404 is inclined with respect to the lower surface of the chamber 201 so as to efficiently exhaust the draft 207. A plurality of protrusions 4041 are provided in the duct 404 in order to reduce the friction of the draft 207. That is, projections and pits substantially exist in the duct 404. The draft 207 is exhausted by the exhaust source 405 at a predetermined angle through the duct 404. Note that a control portion 4051 can arbitrarily change a flow rate and the velocity of flow of air exhausted by the draft exhaust unit 210. In FIG. 4, the draft supply unit 202 and the draft exhaust unit 210 have been described, however, the draft supply units 203 and 204 and the draft exhaust units 208 and 209 have similar structures. In some cases, at least one of the flow rate and the velocity of the flow controlled by at least one of the draft supply unit 202 and the draft exhaust unit 210 is changed in accordance with at least one of the size (more specifically, diameter) of the substrate 103 and the number of rotations of the substrate. The draft supply unit 202 may be a fan filter unit.

Figure 8:
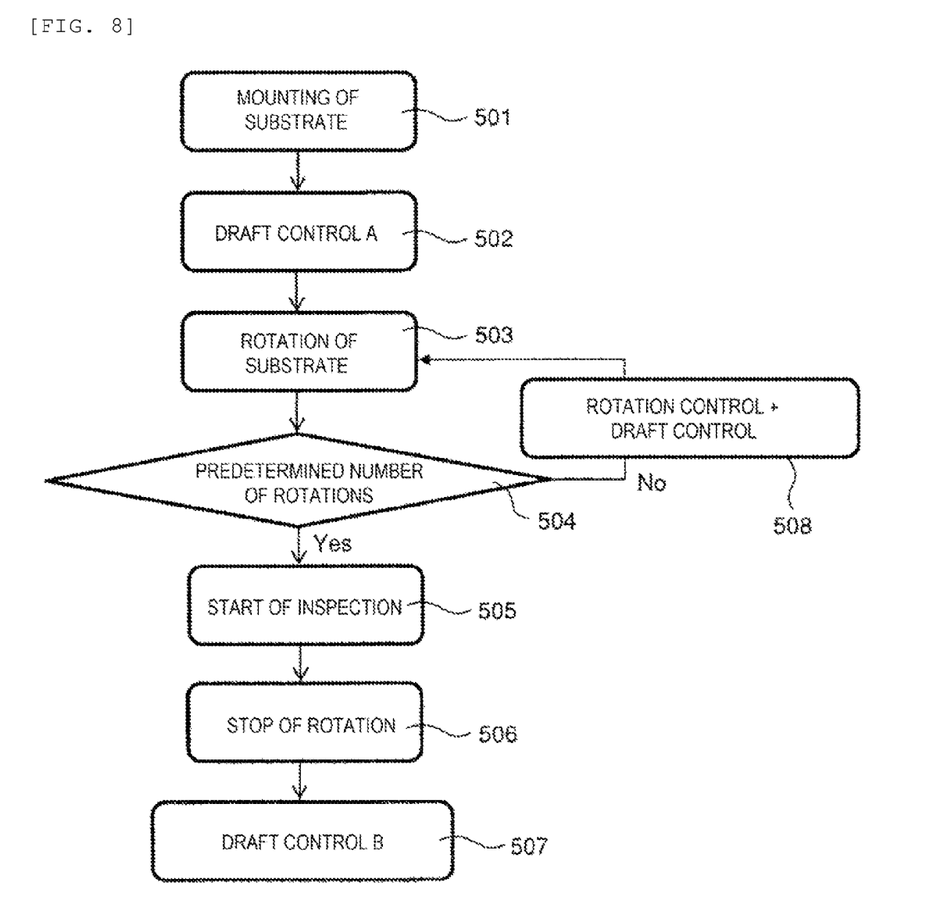
FIG. 8 is a flow chart showing an inspection operation of Example 1.

A flowchart of this example will be described below with reference to FIG. 8. First, the stage 107 is moved downward by control of the processing unit 113. Then, the substrate 103 that has been subjected to pre-alignment in a pre-alignment apparatus which is a former stage of the inspection apparatus is mounted on the substrate mounting unit 104. After the substrate 103 is mounted on the substrate mounting unit 104, the stage 107 is moved upward, and the substrate 103 is housed in the chamber 201 (step 501). Note that supply of the substrate 103 to the stage 107 in the chamber 201 may be carried out by an up-and-down operation (a Z position of the stage 107 is fixed) of a transportation mechanism.

Then, by control of the processing unit 113, the chamber system 105 supplies a draft to the outer regions from above the substrate 103 at a predetermined flow rate and a predetermined velocity of flow of air under a predetermined condition (e.g., presence/absence of the substrate 103, the size of the substrate 103, the number of rotations of the substrate 103) (step 502).

After the processing unit 113 determines that the draft is supplied at the predetermined flow rate and the predetermined velocity of flow, the substrate 103 is rotated by the spindle 106 (step 503).

When the processing unit 113 determines that the number of rotations of the substrate 103 becomes a predetermined number of rotations (e.g., several thousand rpm or more) (step 504), inspection is carried out (step 505). Note that, in a case where the number of rotations of the substrate 103 is not the predetermined number of rotations, the draft is supplied and controlled in conjunction with the number of rotations of the substrate 103 (step 508).

After the inspection of the whole surface of the substrate 103 is completed, the spindle 106 gradually reduces the number of rotations of the substrate 103 and finally stops the rotation of the substrate (step 506).

Thereafter, supply of the draft is returned to the flow rate and the velocity of flow of the draft at the time of supply of the substrate (step 507). Control of the flow rate and the velocity of flow at the time of rotating and moving upward the spindle 106 and control thereof at the time of moving downward the spindle 106 are different in some cases. An operation in the step 501 to the step 507 is repeated for the next substrate.

According to this example, in a case where the substrate 103 is rotated at a high speed, for example, at several thousand rpm, an undesirable draft generated in the outer regions of the substrate 103 and adhesion of particles to the substrate 103 caused by the undesirable draft are effectively reduced by supplying the drafts 205, 206, and 207 to the outer regions from above the substrate 103 and finally exhausting the drafts 205, 206, and 207 to outside of the substrate 103.

Example 2

Example 2 will be described below. In Example 1, the drafts 205, 206, and 207 are supplied from above the chamber 201. This example has a feature that the draft is supplied from the side surface of the chamber 201 and the draft supplied from the side surface of the chamber 201 is exhausted.

Figure 9:
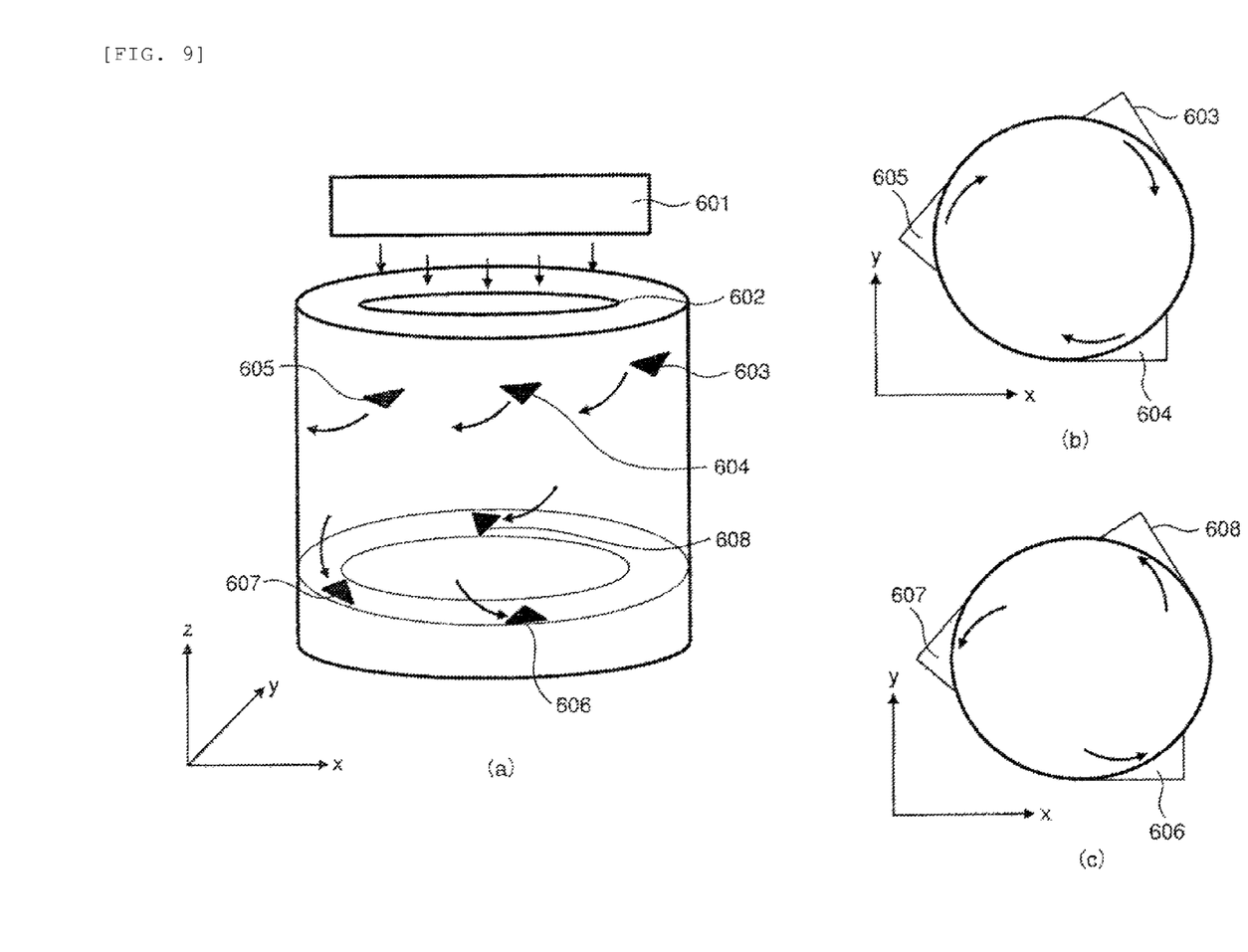
FIGS. 9A-9C illustrate Example 2.

More specifically, this example will be described with reference to FIG. 9. Hereinafter, different parts from those of Example 1 will be mainly described. FIG. 9(a) illustrates the chamber 201 of this example. FIG. 9(b) illustrates arrangement of draft supply units 603, 604, and 605 in a case of observing the chamber 201 of this example from above a Z axis. FIG. 9 (b) illustrates arrangement of draft supply units 606, 607, and 608 in a case of observing the chamber 201 of this example from above the Z axis. The chamber 201 of this example has a substantially tubular shape and has an aperture 602 in the upper surface thereof. Cleaned gas is supplied by a fan filter unit 601 through the aperture 602. The draft supply units 603, 604, and 605 are located on the side surface of the chamber 201. The draft exhaust units 606, 607, and 608 are located at positions lower (as another expression, positions closer to the substrate 103) than positions on which the draft supply units 603, 604, and 605 are located.

Figure 10:
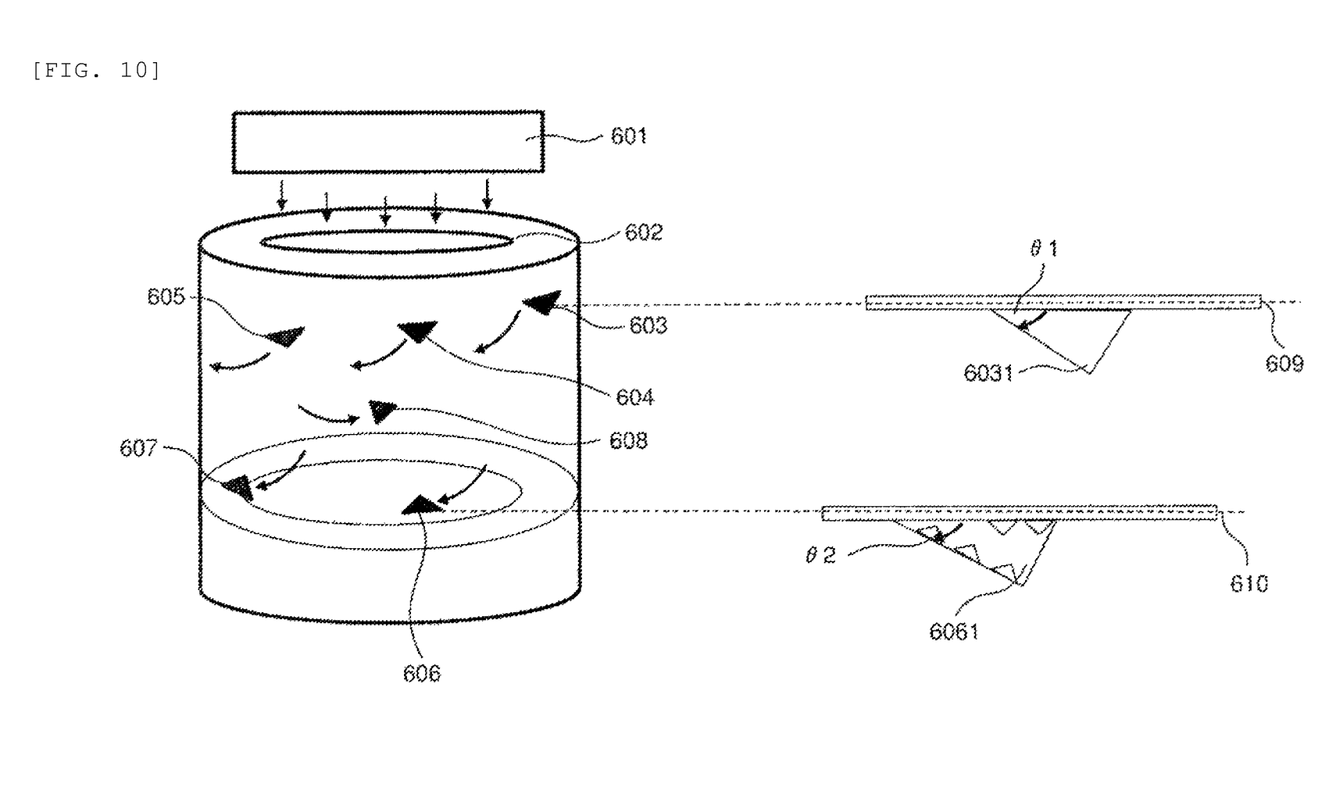
FIG. 10 illustrates Example 2 (continuation).

As illustrated in FIG. 10, a duct 6031 of the draft supply unit 603 is inclined at an angle θ1 with respect to a surface 609 that is in parallel to a cross-section of the chamber 201, and the draft is supplied at the angle θ1. Further, a duct 6061 of the draft exhaust unit 606 is inclined at an angle θ2 with respect to a surface 610 that is in parallel to a cross-section of the chamber 201, and the draft supplied at the angle θ2 is exhausted. The same applies to the draft supply units 604 and 605 and the draft exhaust units 607 and 608. This example obtains an effect similar to that of Example 1.

Figure 11:
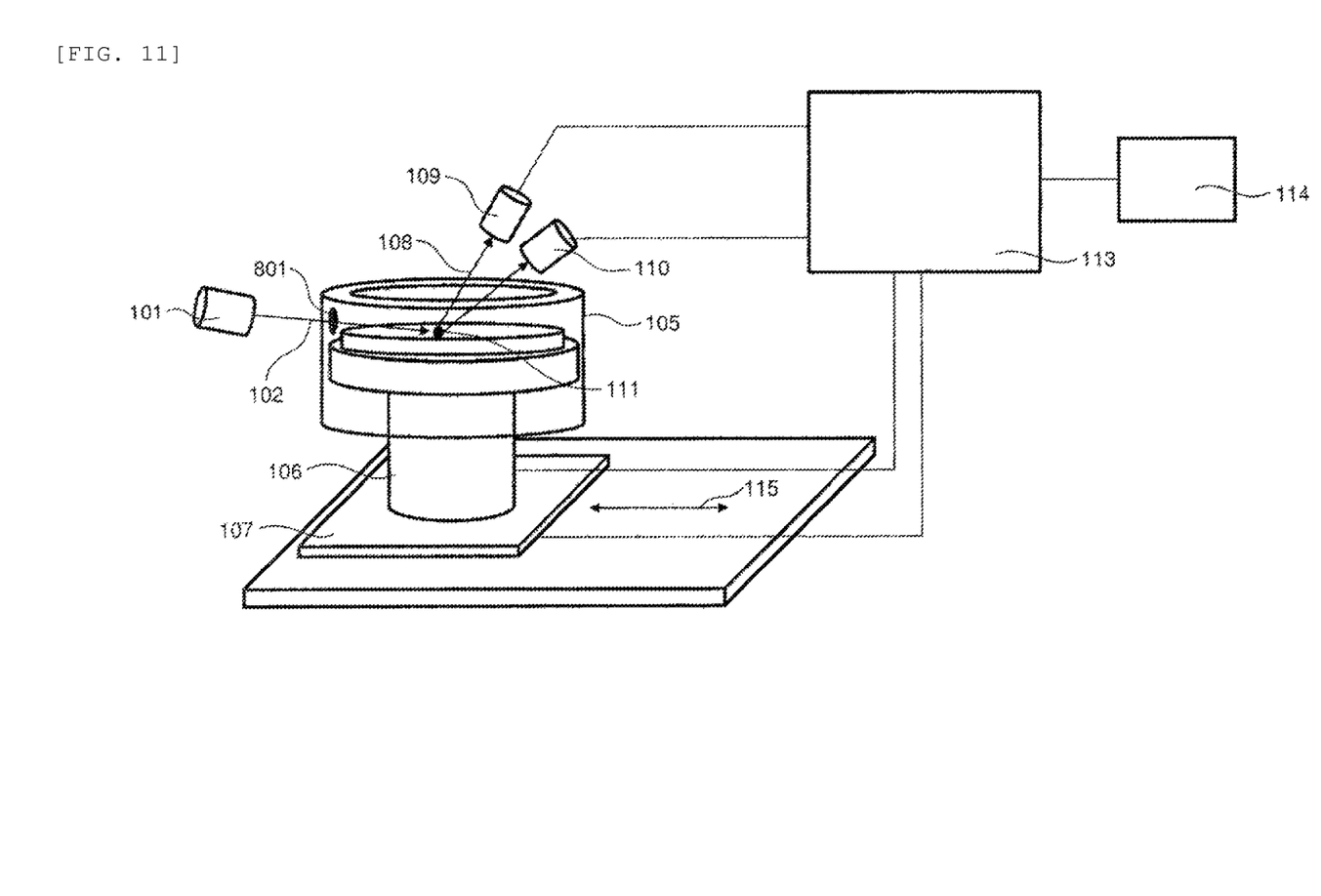
FIG. 11 illustrates a chamber 201 having an aperture 801 in a side surface thereof.

Examples have been described as above, however, the invention is not limited to Examples. For example, as illustrated in FIG. 11, the substrate 103 may be illuminated with the illumination light 102 through an aperture 801 provided in a side wall of the chamber 201. Further, the number of the draft supply units and the number of the draft exhaust units may be larger or smaller than those in Examples. Further, the chamber system 105 of this example may be applied to an apparatus for coating a liquid to a substrate, such as a spin coater.

REFERENCE SIGNS LIST 101 illumination optical system
102 illumination light
103 substrate
104 substrate mounting unit
105 chamber system
106 spindle
107 stage
108 scattered light
109, 110 detection optical system
111 illuminated region
113 processing unit
114 monitor unit
201 chamber
202, 203, and 204 draft supply unit
205, 206, 207 draft
208, 209, and 210 draft exhaust unit
211 aperture
301 lower surface
302 upper surface

The invention claimed is:

1. An inspection apparatus, comprising:
   a spindle for rotating a substrate;
   a chamber for covering at least the substrate;
   a plurality of pairs of an opening and an exhaust in the chamber, each of which supplies a laminar flow to outer regions from above the substrate along an inner surface of the chamber and exhausts the laminar flow on the outside of the substrate; wherein
   each of the plurality of pairs are positioned circumferentially to surround the substrate and to supply and exhaust independent and different laminar flows.

2. The inspection apparatus according to claim 1, further comprising:
   an illumination optical system for irradiating the substrate with light; and
   a detection optical system for detecting the light from the substrate, wherein:
   an aperture is provided in an upper surface of the chamber;
   the illumination optical system irradiates the substrate with the light through the aperture; and
   the detection optical system detects the light from the substrate through the aperture.

3. The inspection apparatus according to claim 2, wherein the substrate is illuminated with the light at a Brewster's angle.

4. The inspection apparatus according to claim 2, wherein the at least one opening is provided outside the aperture on the upper surface.

5. The inspection apparatus according to claim 4, wherein the at least one opening supplies the laminar flow from the upper surface at a an angle.

6. The inspection apparatus according to claim 4, wherein the exhaust is located outside a position on which the substrate is located.

7. The inspection apparatus according to claim 2, wherein the at least one opening is located on a side surface of the chamber.

8. The inspection apparatus according to claim 7, wherein the exhaust is located on the side surface of the chamber and located at a position closer to the substrate than to the at least one opening.

9. The inspection apparatus according to claim 1, wherein a direction of the supplied laminar flow is same as a direction of rotation of the substrate.

10. The inspection apparatus according to claim 1, further comprising:
    an illumination optical system for irradiating the substrate with light; and a detection optical system for detecting the light from the substrate, wherein the illumination optical system and the detection optical system are provided in the chamber and detect the light from the substrate.

11. The inspection apparatus according to claim 10, wherein the at least one opening supplies the laminar flow from an upper surface of the chamber at an angle.

12. The inspection apparatus according to claim 10, wherein the exhaust is located outside a position on which the substrate is located.

13. The inspection apparatus according to claim 10, wherein the at least one opening is provided on a side surface of the chamber.

14. The inspection apparatus according to claim 13, wherein the exhaust is located on the side surface of the chamber and is located at a position closer to the substrate than to the at least one opening.

15. The inspection apparatus according to claim 1, wherein a direction of the supplied laminar flow is same as a direction of rotation of the substrate.

16. The inspection apparatus according to claim 1, wherein the number of the pairs is three.

17. An inspection apparatus, comprising:

a spindle for rotating a substrate;

a chamber for covering at least the substrate;

a plurality of pairs of an opening and an exhaust in the chamber, each of which supplies a conductor to outer regions from above the substrate along an inner surface of the chamber and exhausts the conductor on the outside of the substrate; and wherein flow directions of each conductor are along the spin direction of the spindle; and wherein each of the plurality of pairs are positioned circumferentially to surround the substrate and to supply and exhaust independent and different laminar flows.

18. The inspection apparatus according to claim 17, wherein the number of the pairs is three.

* * * * *